United States Patent [19]

Payne

[11] 4,166,131
[45] Aug. 28, 1979

[54] INDANEACETIC ACID DERIVATIVES
[75] Inventor: Trevor G. Payne, Arlesheim, Switzerland
[73] Assignee: Hexachimie Société Anonyme, Rueil Malmaison, France
[21] Appl. No.: 517,531
[22] Filed: Oct. 24, 1974
[30] Foreign Application Priority Data
Oct. 30, 1973 [CH] Switzerland .................. 15251/73
[51] Int. Cl.$^2$ .................. C07C 63/337; C07C 69/76; A61K 31/19; A61K 31/215
[52] U.S. Cl. .................. 424/317; 560/8; 560/51; 560/60; 560/104; 560/105; 562/405; 562/459; 562/470; 562/495; 562/496; 260/465 R; 260/590 FA; 424/308; 568/808
[58] Field of Search .............. 260/515 R, 469, 515 A; 424/308, 317; 560/8
[56] References Cited
U.S. PATENT DOCUMENTS
4,058,622  11/1977  Fujimoto et al. .................. 560/8

Primary Examiner—Jane S. Myers
Attorney, Agent, or Firm—Bacon & Thomas

[57] ABSTRACT

This invention provides new compounds of formula I,

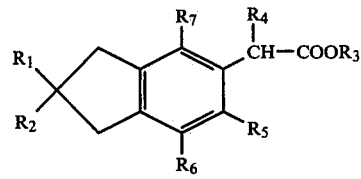

wherein
$R_1$ is lower alkyl,
$R_2$ is hydrogen or lower alkyl,
$R_3$ is hydrogen or lower alkyl,
$R_4$ is hydrogen or lower alkyl,
$R_5$ is hydrogen, chlorine or lower alkyl, and each of $R_6$ and $R_7$ is hydrogen, or, when $R_5$ is hydrogen, $R_6$ may also be chlorine or lower alkyl, and $R_7$ chlorine or lower alkyl, useful as anti-phlogistic and anti-arthritic agents.

40 Claims, No Drawings

INDANEACETIC ACID DERIVATIVES

The present invention relates to new heterocyclic compounds.

In accordance with the invention there are provided new compounds of formula I,

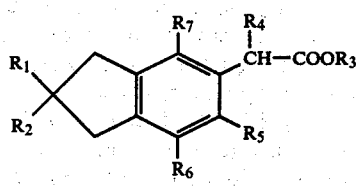

wherein
- $R_1$ is lower alkyl,
- $R_2$ is hydrogen or lower alkyl,
- $R_3$ is hydrogen or lower alkyl,
- $R_4$ is hydrogen or lower alkyl,
- $R_5$ is hydrogen, chlorine or lower alkyl, and each of $R_6$ and $R_7$ is hydrogen, or, when $R_5$ is hydrogen, $R_6$ may also be chlorine or lower alkyl, and $R_7$ chlorine or lower alkyl.

Further, in accordance with the invention a compound of formula I may be obtained by a process comprising (a) reducing a compound of formula II,

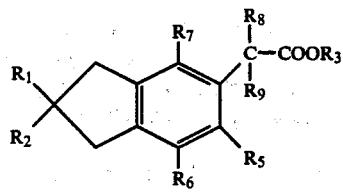

wherein
$R_1$, $R_2$, $R_3$, $R_5$, $R_6$ and $R_7$ are as defined above, and
$R_8$ and $R_9$ together are oxygen or lower alkylidene, or
$R_8$ is hydrogen or lower alkyl and
$R_9$ is hydroxyl, or (b) converting the CN group into the COOR$_3$ group, wherein $R_3$ is as defined above, in a compound of formula III,

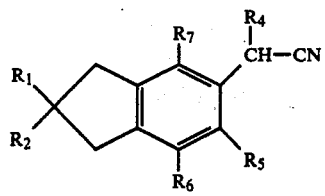

wherein $R_1$, $R_2$, $R_4$, $R_5$, $R_6$ and $R_7$ are as defined above, or (c) alkylating a compound of formula Ia,

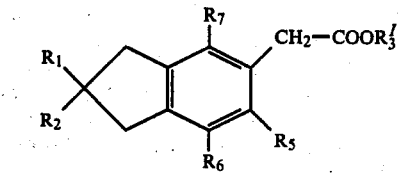

wherein
$R_1$, $R_2$, $R_5$, $R_6$ and $R_7$ are as defined above, and
$R_3{}^I$ is lower alkyl,
with a compound of formula IV, $$R_4{}^I\!-\!X \qquad \text{IV}$$

wherein
$R_4{}^I$ is lower alkyl, and
X is the acid radical of a reactive ester, or (d) hydrolyzing a compound of formula Ib,

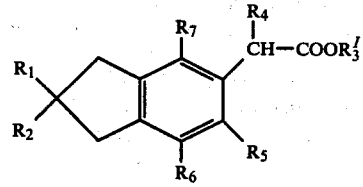

wherein
$R_1$, $R_2$, $R_3{}^I$, $R_4$, $R_5$, $R_6$ and $R_7$ are as defined above, to produce a compound of the formula Ic,

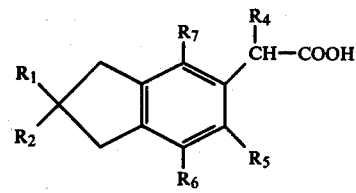

wherein
$R_1$, $R_2$, $R_4$, $R_5$, $R_6$ and $R_7$ are as defined above, or (e) reacting a compound of formula XX,

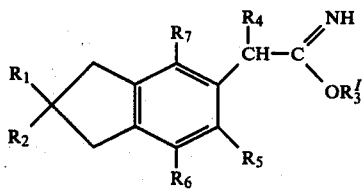

wherein
$R_1$, $R_2$, $R_3{}^I$, $R_4$, $R_5$, $R_6$ and $R_7$ are as defined above, with water to produce a compound of formula Ib as defined above.

The lower alkyl group represented by the symbol $R_1$ in the compounds of formula I preferably contains 1 to 4 carbon atoms and especially signifies methyl or ethyl. When $R_2$ is lower alkyl, this preferably contains 1 to 4 carbon atoms. $R_2$ preferably denotes hydrogen or methyl. $R_3$ preferably denotes hydrogen. When $R_3$ is lower alkyl, this preferably contains 1 to 4 carbon atoms and may, for example, signify methyl, ethyl, isopropyl or tert.butyl. When $R_4$ is lower alkyl, this preferably contains 1 to 4 carbon atoms. $R_4$ preferably signifies methyl or hydrogen. $R_6$ and $R_7$ preferably signify hydrogen, and $R_5$ hydrogen or chlorine. When $R_5$, $R_6$ or $R_7$ is lower alkyl, this alkyl group preferably contains 1 to 4 carbon atoms and especially signify methyl. The preferred compounds are those wherein $R_1$ is methyl, ethyl or isopropyl and $R_2$ is hydrogen or methyl, $R_3$ is hydrogen and $R_4$ is methyl or hydrogen, and each of $R_5$, $R_6$ and $R_7$ is hydrogen.

Any carbon-containing radical used herein and not otherwise particularly defined preferably has up to 4 carbon atoms.

The reduction of compounds of formula II may be effected in accordance with known methods. A suitable reduction process is, for example, catalytic hydrogenation. Hydrogenation may, for example, be effected under a hydrogen pressure between 1 and 5 atmospheres. A temperature between 10° and 100° C. preferably below reflux temperature, may be used. Suitable catalysts are platinum or palladium catalysts or Raney nickel. Examples of suitable solvents are lower alcohols e.g. methanol or ethanol or mixtures of alcohol/water. When $R_3$ in the compound of formula II is hydrogen, acetic acid is a convenient solvent. Hydrogenation is preferably effected with the addition of a strong mineral acid, e.g. sulphuric or perchloric acid. An acid of formula II ($R_3$=hydrogen) wherein $R_8$ and $R_9$ together form an alkylidene group, and $R_5$, $R_6$ and $R_7$ signify other than chlorine, may alternatively be reduced to a corresponding acid of formula I ($R_3$=hydrogen, $R_4$=lower alkyl), for example by treatment with sodium in liquid ammonia or a lower alcohol such as propanol, n-butanol or methylisobutyl carbinol. The reduction of compounds of formula II wherein $R_8$ and $R_9$ together are oxygen, may alternatively be effected, for example, in accordance with the method of Wolff-Kishner and modifications thereof, whereby acids of formula I ($R_3$=hydrogen, $R_4$=hydrogen) are obtained. Thus, in accordance with Wolff-Kishner a compound of formula II may first be converted into a hydrazone thereof and this may subsequently be hydrolysed with a strong base, for example an alkali metal hydroxide or alcoholate. The Wolff-Kishner reduction is preferably effected in accordance with the process variant of Huang-Minlon, for example by allowing to react a compound of formula II with hydrazine hydrate in the presence of an alkali metal hydroxide, e.g. sodium or potassium hydroxide, and an inert, high-boiling, polar, water-miscible organic solvent, is conveniently present. Examples of suitable solvents are polyalcohols such as diethylene or triethylene glycol, or dimethyl sulphoxide. A temperature of between about 20° and about 220° C. is conveniently used.

The solvolysis of the compounds of formula III in accordance with process variant (b) may be effected in known manner. For example, a compound of formula III may be allowed to react with water or a mixture of an alcohol of formula V, $$R_3{}^I\text{—OH} \qquad \qquad V$$

wherein $R_3{}^I$ is as defined above, and water. The reaction may, for example, be effected in the presence of a strongly acid catalyst, for example a strong mineral acid such as concentrated hydrochloric acid, e.g. 20 to 75%, sulphuric acid or phosphoric acid, or a strong organic acid, e.g. an organic sulphonic acid. Alternatively there may be used a strongly basic catalyst, e.g. an alkali metal hydroxide solution, e.g. a 10 to 50%, sodium or potassium hydroxide solution. For the direct conversion of the CN group into the carboxyl group, a compound of formula III may, for example by hydrolyzed with two equivalents of water. With an acid catalyst a temperature between 60° and 120° C., preferably the reflux temperature of the reaction mixture may be used. With a basic catalyst a temperature between 20° and 150° C. may be used. An inert organic water-miscible solvent, e.g. an alcohol such as methanol, ethanol, amyl alcohol or ethylene glycol, or an ether such as dioxane may be used. Alternatively acetic acid may be used in the presence of an acid catalyst. The conversion of the CN group into an ester group may be effected by reacting the compound of formula III with an alcohol $R_3{}^I$—OH containing an amount of water preferably equivalent to the amount of compound of formula III used. There may be present a further solvent as indicated above. An acid or basic catalyst may be present. A suitable temperature is between about 50° and 100° C.

If desired, the compounds of formula III may first be converted with an alcohol into the corresponding imino ethers, and these may subsequently be hydrolyzed to the esters with a preferably equivalent amount of water.

Process variant (c) may be effected in conventional manner for α-alkylation of such indan-acetic acid esters. X is preferably halogen or a mesyloxy or tosyloxy group. An inert solvent, e.g. an aromatic hydrocarbon such as toluene or benzene, or an ether, e.g. tetrahydrofuran, dioxane or diethyl ether is preferably used. A basic condensation agent, e.g. lithium diisopropylamide or sodium amide or hydride, is conveniently used. A suitable temperature is between about −70° and +100° C.

Process variant (d) may be effected in coventional manner for hydrolysis of such esters. For example the reaction conditions indicated above under process variant (b) for the production of acids of formula I may be used.

Process variant (e) may be effected in conventional manner for the conversion of such imino ethers into esters. For example of reaction conditions indicated above under process variant (b) for the production of esters of formula I may be used.

The resulting compounds of formula I may be isolated from the reaction mixture and purified in known manner.

The starting materials may, for example, be obtained as follows:

(a') A compound of formula IIa,

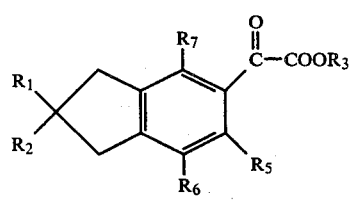

wherein $R_1$, $R_2$, $R_3$, $R_5$, $R_6$ and $R_7$ are as defined above, may, for example, be obtained by (i) reacting a compound of formula VIII,

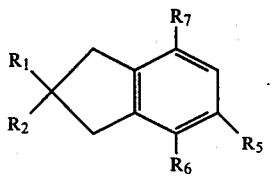    VIII wherein

R₁, R₂, R₅, R₆ and R₇ are as defined above,
with an oxalic acid monoalkyl ester chloride of formula VI,

    VI wherein $R_3^I$ is as defined above, in the presence of an acid catalyst, to produce an ester of formula IIa wherein $R_3$ is $R_3^I$ as defined above; or (ii) by hydrolyzing an ester of formula II wherein $R_3$ is $R_3^I$ as defined above to produce an acid of formula II wherein $R_3$ is H. The reaction of a compound of formula VIII with an oxalic acid monoalkyl ester chloride is preferably effected under the conditions of a Friedel-Crafts reaction, e.g. in the presence of aluminium trichloride. An inert organic solvent, e.g. carbon disulphide, or a halogenated hydrocarbon, e.g. methylene chloride may be used. A suitable temperature is between 0° and the boiling temperature of the reaction mixture.

(b′) A compound of formula IIb,

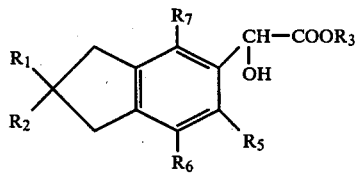    IIb wherein

R₁, R₂, R₃, R₅, R₆ and R₇ are as defined above,
may, for example, be obtained by reducing a compound of formula IIa with sodium borohydride. The reduction is preferably effected in a lower alcohol, e.g. methanol or ethanol.

(c′) A compound of formula IIc,

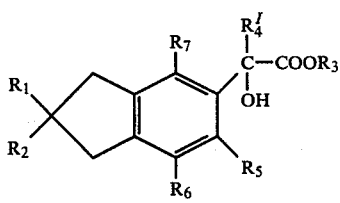    IIc wherein

R₁, R₂, R₃, R₄$^I$, R₅, R₆ and R₇ are as defined above, may, for example, be obtained by (i) reacting an ester of formula IIa (R₃=lower alkyl) with a Grignard compound of formula VII,

    VII wherein

R₄$^I$ is as defined above, and

X is chlorine, bromine or iodine,
in an inert solvent, to produce an ester of formula IIc wherein R₃ is R₃$^I$ as defined above, or (ii) hydrolyzing an ester of formula IIc wherein R₃ is R₃$^I$ as defined above to produce an acid of formula IIc wherein R₃ is H.

For process (i) a suitable solvent is e.g. an ether such as diethyl ether or tetrahydrofuran. A suitable temperature is between about 0° and 50° C.

For process variant (ii) conventional hydrolysis conditions may be used, e.g. alkaline conditions.

(d′) A compound of formula IId,

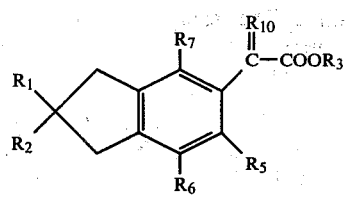    IId wherein

R₁, R₂, R₃, R₅, R₆ and R₇ are as defined above, and
R₁₀ is alkylidene,
may, for example, be obtained by removing water from a compound of formula IIc. For example there may be used a catalytic amount of a strong acid, e.g. methanesulphonic acid or p-toluenesulphonic acid. An inert solvent, e.g. a hydrocarbon such as benzene or toluene may be used. There may be used an elevated temperature, preferably the boiling temperature of the reaction mixture.

(e′) A compound of formula IIIa,

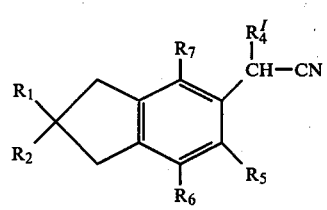    IIIa wherein

R₁, R₂, R₄$^I$, R₅, R₆ and R₇ are as defined above,
may, for example, be obtained by reacting a compound of formula IIIb,

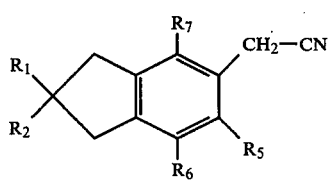    IIIb wherein

R₁, R₂, R₅, R₆ and R₇ are as defined above,
with a, preferably equivalent, amount of a compound of formula IV. The reaction may, for example, be effected under the reaction conditions described for the alkylation of a compound of formula Ia.

(f′) A compound of formula III may, for example, be obtained by reacting a compound of formula IX,

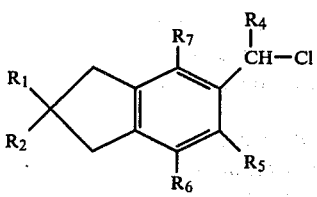

wherein

R₁, R₂, R₄, R₅, R₆ and R₇ are as defined above,
with a metal cyanide. It is preferred to use an alkali metal cyanide such as sodium or potassium cyanide, or copper-(I)-cyanide. The reaction may, for example, be effected in an inert solvent such as water, acetone, a lower alcohol or dimethyl formamide, or a mixture of water and one of these organic solvents. There may be present a metal iodide such as sodium or potassium iodide. The reaction temperature may be between 10° and 150° C., preferably between 50° and 120° C.

(g') A compound of formula IX may, for example, be obtained by chloroalkylating a compound of formula VIII, for example by allowing to react a mixture of a compound of formula VIII and an aldehyde of formula X,

  R₄—CHO  X wherein R₄ is as defined above,
or a polymer thereof. The reaction may be effected in an acid solution, e.g. in aqueous hydrochloric acid or in acetic acid, while passing through hydrogen chloride gas, or in a concentrated hydrochloric acid solution. A suitable temperature is between about −20° and +80° C., preferably −10° and +15° C.

(h') A compound of formula VIII may, for example, be obtained by reducing a compound of formula XII,

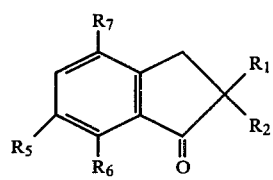  XII wherein R₁, R₂, R₅, R₆ and R₇ are as defined above, obtainable
by cyclizing a compound of formula XI,

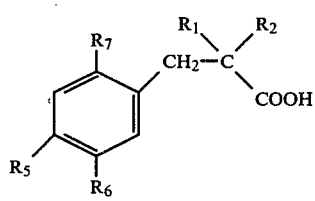  XI wherein R₁, R₂, R₅, R₆ and R₇ are as defined above, or a reactive acid derivative thereof.

The reduction of a compound of formula XII may, for example, be effected with nascent hydrogen, e.g. by treating a compound of formula XII with amalgamated zinc/concentrated hydrochloric acid in accordance with the method of Clemmensen.

Alternatively a compound of formula XII may be catalytically hydrogenated. A suitable catalyst is palladium charcoal. A suitable solvent is an aqueous alcoholic solution of a mineral acid, e.g. hydrochloric acid.

The cyclization of a compound of formula XI is preferably effected in the presence of a strongly acid catalyst, e.g. a mineral acid, preferably hydrofluoric acid or polyphosphoric acid or sulphuric acid. There may be present an inert organic solvent, e.g. a hydrocarbon such as benzene, toluene or tetraline. The cyclization may alternatively be effected with a reactive derivative of an acid of formula XI. Examples of suitable reactive derivatives are the acid halides. In accordance with a process variant, an acid of formula XI may, for example, be first converted into an acid chloride thereof with an inorganic acid chloride, e.g. thionyl chloride. The acid chloride may subsequently be cyclized under the reaction conditions of a Friedel Crafts reaction in the presence of a Friedel-Crafts catalyst, e.g. aluminium chloride, in an inert organic solvent.

(i') A compound of formula VIIIa,

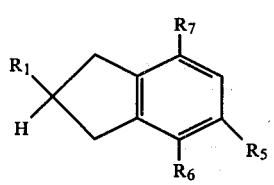  VIIIa wherein R₁, R₅, R₆ and R₇ are as defined above, may, for example, be obtained by reducing a compound of formula XVa

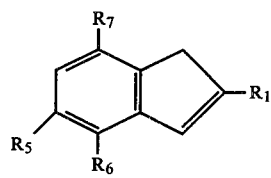  XVa wherein R₁, R₅, R₆ and R₇ are as defined above, and/or a compound of formula XVb

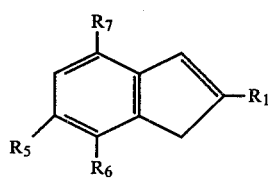  XVb wherein R₁, R₅, R₆ and R₇ are as defined above, obtainable by removing water from a compound of formula

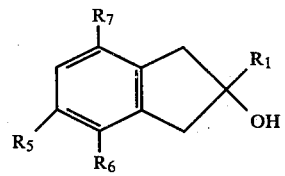

wherein R₁, R₂, R₅, R₆ and R₇ are as defined above, which in turn is obtainable by reacting a compound of formula XIII,

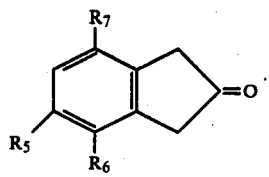

wherein R₅, R₆ and R₇ are as defined above,
with a Grignard compound of formula XIV,

 XIV wherein R₁ is as defined above.
The reduction of a compound of formula XVa and/or XVb is preferably effected by catalytic hydrogenation.

(j') A compound of formula XIa,

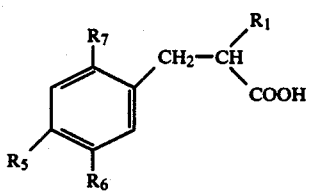 XIa wherein R₁, R₅, R₆ and R₇ are as defined above,
may, for example, be obtained by hydrogenating a compound of formula

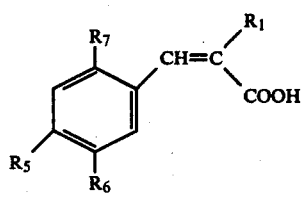

wherein R₁, R₅, R₆ and R₇ are as defined above,
obtainable by hydrolyzing a compound of formula

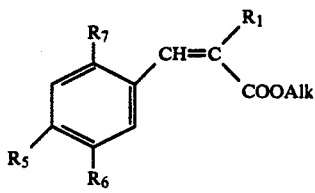

wherein R₁, R₅, R₆ and R₇ are as defined above, and Alk is lower alkyl,
which is in turn obtainable by condensing an aldehyde of formula XVI

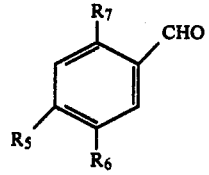 XVI wherein R₅, R₆ and R₇ are as defined above,
with a compound of formula XVII,

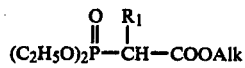 XVII wherein R₁ and Alk are as defined above,
with the addition of a strong base, e.g. an alkali metal alcoholate. The reduction of the double bond may be effected either by catalytic hydrogenation or, when R₅, R₆ and R₇ are other than chlorine, also with nascent hydrogen, by treating the compound with sodium metal in alcohol, e.g. methyl isobutylcarbinol. A solvent e.g. toluene may be present. An elevated temperature e.g. 130° may be used.

(k') A compound of formula XIb,

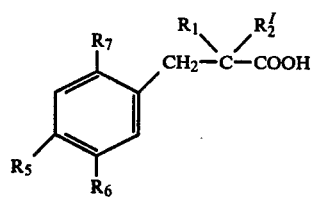 XIb wherein R₁, R₅, R₆ and R₇ are as defined above, and R₂ᴵ is lower alkyl,
may, for example, be obtained by saponifying a compound of the formula

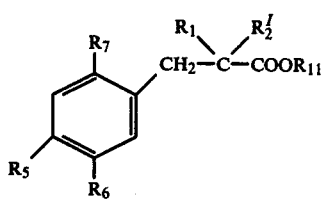

wherein
R₁, R₂ᴵ, R₅ R₆ and R₇ are as defined above, and
R₁₁ is lower alkyl,
obtainable by condensing a compound of formula XVIII,

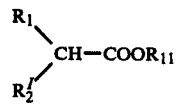 XVIII wherein
R₁ and R₂ᴵ are as defined above, and
R₁₁ is lower alkyl,
with a halogen compound of formula XIX,

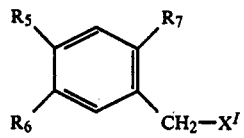 XIX wherein R₅, R₆, R₇ and Xᴵ are as defined above.
The reaction may be effected in a strong base, e.g. sodium hydride or amide. An inert organic solvent, e.g. an ether such as tetrahydrofuran may be used.

Insofar as the above processes are not specifically described these may be effected in conventional manner for such processes, bearing in mind the type of starting material used and the substitutents present in the starting material.

Insofar as the production of the starting materials e.g. indanes substituted at the 2 position with alkyl, is not described, these are known or may be produced in accordance with known processes, or in a manner analogous to the processes described herein or to known processes.

Free acid forms of compounds of formula Ic may be converted into salt forms in conventional manner and vice-versa. Suitable salt forms include the (1,3-dihydroxy-2-hydroxymethyl-2-propyl) ammonium salt and the cyclohexyl-ammonium salt.

In the following non-limitative Examples all temperatures are indicated in degrees Centigrade.

EXAMPLE 1

2-isopropyl-α-methyl-5-indanacetic acid [process variant (a)]

A solution of 15 g of α-hydroxy-2-isopropyl-α-methyl-5-indanacetic acid in 300 cc of glacial acetic acid and 4 cc of 70% perchloric acid is hydrogenated at 80°, while stirring, for 15 hours, with the addition of 400 mg of a platinum(IV) oxide catalyst. The solution is subsequently filtered, 6 g of anhydrous sodium acetate are added thereto, and the solvent is removed by evaporation. The residue is distributed between ether and water, the ether phase is washed with water, dried over sodium sulphate, filtered and concentrated. The resulting 2-isopropyl-α-methyl-5-indanacetic acid is purified by chromatography on silica gel and recrystallized from hexane. M.P. 83°–86°.

The 2-isopropyl-α-methyl-5-indanacetic acid (1,3-dihydroxy-2-hydroxymethyl-2-propyl)ammonium salt, obtained by reaction with 2-amino-2-hydroxy-methyl-1,3-propanediol, crystallizes from methanol/ether and has a M.P. of 140°–141°.

The starting material may be obtained as follows:

(a) 36 g of indan-2-carboxylic acid (produced from αα'-dibromo-o-xylene and malonic acid dimethyl ester) are dissolved in 500 cc of methanol, and hydrogen chloride gas is passed through the solution at 20°–35° for 5 hours, while stirring. The solution is concentrated and the resulting, crude indan-2-carboxylic acid methyl ester is purified by distillation in a bulb tube distilling apparatus. B.P. 150°–170° at 11 mm of Hg.

(b) A solution of 37.3 g of indan-2-carboxylic acid methyl ester in 200 cc of ether is added dropwise to a solution of methyl magnesium iodide (produced from 142 g of methyl iodide and 24.0 g of magnesium shavings) in 1.2 liters of ether and the mixture is boiled at reflux for 2 hours. 500 cc of a 10% ammonium chloride solution are then carefully added to the reaction mixture and this is extracted with ether. The ether extract is washed with water, dried over sodium sulphate and concentrated by evaporation. The resulting, crude 2-(2-indanyl)-2-propanol is taken up in one liter of toluene and boiled at reflux for 24 hours together with 1 g of p-toluenesulphonic acid. The cooled solution is washed with sodium bicarbonate solution, dried over sodium sulphate and concentrated. The resulting oil is taken up in 500 cc of ethanol and hydrogenated at room temperature under pressure with the addition of 1 g of 10% palladium/charcoal. The solution is filtered and concentrated. The resulting 2-isopropyl-indan has a M.P. of 40°–41°.

(c) A solution of 33 g of 2-isopropyl-indan and 27.8 g of oxalic acid monomethyl ester chloride in 400 cc of methylene chloride is added dropwise within 60 minutes to a suspension of 55 g of aluminium chloride in 400 cc of methylene chloride at 0°–5°, while stirring. The red solution is stirred at room temperature for a further 3 hours and is then poured on ice/water. The mixture is extracted with methylene chloride, the extract is filtered through talc, washed with water, dried over sodium sulphate and concentrated. The resulting 2-isopropyl-α-oxo-5-indanacetic acid methyl ester is purified by distillation in a bulb tube. B.P.: 200° at 0.2 mm of Hg.

(d) A solution of 41 g of 2-isopropyl-α-oxo-5-indanacetic acid methyl ester in 400 cc of ether is added dropwise to a solution of methyl-magnesium iodide (produced from 9.6 g of magnesium shavings and 25 cc of methyl iodide) in 500 cc of ether, and the mixture is stirred at reflux for 2 hours. 400 cc of a 10% ammonium chloride solution are added dropwise to the cooled reaction mixture and extraction with ether is subsequently effected. The ether extract is washed with water, dried over sodium sulphate and concentrated by evaporation. The resulting crude α-hydroxy-2-isopropyl-α-methyl-5-indanacetic acid methyl ester is used for the next reaction without purification.

(e) A solution of 26.6 g of potassium hydroxide in 50 cc of water is added to a solution of 41.5 g of crude α-hydroxy-2-isopropyl-α-methyl-5-indanacetic acid methyl ester in 500 cc of methanol, and the mixture is boiled at reflux for 1½ hours. The solution is concentrated, diluted with water and extracted with ether in order to remove the neutral components. The aqueous phase is then acidified with hydrochloric acid, extracted with ether, the ether extract is washed with water, dried over sodium sulphate and concentrated by evaporation. The resulting α-hydroxy-2-isopropyl-α-methyl-5-indanacetic acid is recrystallized from ether/hexane and has a M.P. of 126°–130°.

EXAMPLE 2

2-isopropyl-α-methyl-5-indanacetic acid

A solution of 1.7 g of 2-isopropyl-α-methylene-5-indanacetic acid in 300 cc of ethanol is hydrogenated at room temperature with the addition of 50 mg of platinum(IV) oxide. After filtering off the catalyst, removing the solvent by evaporation and chromatographing the resulting oil, 2-isopropyl-α-methyl-5-indanacetic acid, having a M.P. of 83°–86°, is obtained. The (1,3-dihydroxy-2-hydroxymethyl-2-propyl)ammonium salt of the title compound has a M.P. of 140°–141° (from methanol/ether).

The starting material may be obtained as follows:

A solution of 3.8 g of α-hydroxy-2-isopropyl-α-methyl-5-indanacetic acid in 300 cc of toluene is boiled at reflux (water separator) together with 0.5 g of p-toluenesulphonic acid for 5 hours. The cooled solution is washed with water, dried over sodium sulphate and concentrated. The resulting 2-isopropyl-α-methylene-5-indanacetic acid is recrystallized from toluene/hexane and has a M.P. of 158°–159°.

EXAMPLE 3

2-ethyl-2,α-dimethyl-5-indanacetic acid 2-ethyl-α-hydroxy-2,α-dimethyl-5-indanacetic acid is hydrogenated in a manner analogous to that described in Example 1. The cyclohexyl-ammonium salt of the title compound has a M.P. of 165°–167° (from ether).

The starting material may be obtained as follows:

(a) 202.7 g of α-methyl-butyric acid methyl ester are added dropwise to a suspension of 44 g of sodium hydride in 1.3 liters of tetrahydrofuran and the mixture is subsequently boiled at reflux with stirring for 16 hours. A solution of 204 cc of benzyl chloride in 500 cc of tetrahydrofuran is then added dropwise and the reaction mixture is boiled at reflux for a further 70 hours. Working up is effected by removing the tetrahydrofuran by distillation, cooling the mixture, adding 600 cc of petroleum ether and 30 cc of methanol, washing with 300 cc of 5% acetic acid and then with water. The crude, oily α-ethyl-α-methyl-dihydrocinnamic acid methyl ester, obtained after evaporating the solvent, is distilled at 15 mm of Hg and the fraction boiling at 130°–140° is used for the next reaction step without further purification.

(b) A solution of 100 g of potassium hydroxide in 200 cc of water is added to a solution of 101.5 g of α-ethyl-α-methyl-dihydrocinnamic acid methyl ester in 1.5 liters of methanol, and the reaction mixture is boiled at reflux for 20 hours. The solution is concentrated to a volume of about 300 cc, is diluted with water and the neutral by-products are extracted with ether. The aqueous phase is then acidified with hydrochloric acid, extracted with ether, the ether extract is washed with water, dried over sodium sulphate and concentrated by evaporation. The resulting oily, crude α-ethyl-α-methyl-dihydrocinnamic acid may be purified by chromatography.

(c) 69 g of α-ethyl-α-methyl-dihydrocinnamic acid are added dropwise at 150°, within 5 minutes, to 700 g of polyphosphoric acid, while stirring. The reaction mixture is stirred at 160° for a further 10 minutes, is cooled to 100° and 100 cc of water are added dropwise. The reaction mixture is then poured on ice, extracted with ether, the ether extract is washed with water and dried over sodium sulphate. The 2-ethyl-2-methyl-1-indanone, obtained after evaporating the solvent, is purified by distillation. B.P. 137°–140° at 20 mm of Hg.

(d) 335 g of zinc dust and 33.5 g of mercury (II) acetate and a solution of 330 cc of concentrated hydrochloric acid in 280 cc of water are rapidly added dropwise in a stirring apparatus. The mixture is boiled at reflux and a solution of 63 g of 2-ethyl-2-methyl-1-indanone in 525 cc of ethanol is added dropwise within 10 minutes while stirring. The reaction mixture is subsequently stirred at reflux for 28 hours, cooled, filtered, and the residue is washed with water/petroleum ether. The filtrate is extracted with petroleum ether, the petroleum ether extract is washed with water and dried over sodium sulphate. The crude 2-ethyl-2-methyl-indan, obtained as an oil after evaporating the solvent, is purified by chromatography on aluminium oxide/petroleum ether.

(e) 2-ethyl-α-oxo-2-methyl-5-indanacetic acid methyl ester is produced in a manner analogous to that described in Example 1(c) and used for the next reaction in crude state.

(f) 2-ethyl-α-hydroxy-2,α-dimethyl-5-indanacetic acid is produced in a manner analogous to that described in Example 1(d) and 1(e) and used for the next reaction in crude state.

EXAMPLE 4

2-ethyl-2,6-dimethyl-5-indanacetic acid 10 g of potassium hydroxide are added to a solution of 6.2 g of 2-ethyl-2,6-dimethyl-α-oxo-5-indanacetic acid methyl ester in 50 cc of diethylene glycol, the reaction mixture is stirred at 100° for one hour and is then allowed to stand for 12 hours. 12 cc of hydrazine hydrate are subsequently added, the mixture is heated at reflux for one hour while stirring, the excess hydrazine hydrate and the water formed during the reaction are distilled off until the boiling temperature of the reaction mixture rises to 180°, and then boiling at reflux is effected at 180° for a further two hours. The reaction mixture is cooled to room temperature, diluted with water, acidified with hydrochloric acid and extracted with ether. The extract is washed with water, dried over sodium sulphate and concentrated by evaporation. The resulting 2-ethyl-2,6-dimethyl-5-indanacetic acid is recrystallized from petroleum ether at −30° and has a M.P. of 40°–42°. The cyclohexylammonium salt of the title compound has a M.P. of 154°–156°.

The starting material may be obtained as follows:

(a) α-ethyl-α,4-dimethyl-dihydrocinnamic acid methyl ester is produced in a manner analogous to Example 3(a), from α-methyl-butyric acid methyl ester and α-bromo-p-xylene. B.P. 135°–152° at 13 mm of Hg.

(b) α-ethyl-α,4-dimethyl-dihydrocinnamic acid is produced in a manner analogous to Example 3(b); oily crude product, used as such for the next reaction.

(c) 2-ethyl-2,6-dimethyl-1-indanone is produced in a manner analogous to Example 3(c). M.P. 25.5°–27°.

(d) 2-ethyl-2,5-dimethyl-indan is produced in a manner analogous to Example 3(d); oily crude product, used as such for the next reaction.

(e) 2-ethyl-60-oxo-2,6-dimethyl-5-indanacetic acid methyl ester is produced in a mannner analogous to Example 1(c). B.P. 195° at 0.1 mm of Hg.

EXAMPLE 5

2-isopropyl-5-indanacetic acid 2-isopropyl-α-oxo-5-indanacetic acid is reduced in a manner analogous to that described in Example 4, by reaction with potassium hydroxide and hydrazine hydrate. The title compound has an M.P. of 83°–86°.

The starting material may be obtained as follows:

(a) 2-isopropyl-α-oxo-5-indanacetic acid ethyl ester is produced in a manner analogous to Example 1(c). The oily crude product is used as such for the next reaction.

(b) A solution of 10 g of sodium hydroxide in 20 cc of water is added to a solution of 24.5 g of crude 2-isopropyl-α-oxo-5-indanacetic acid ethyl ester in 300 cc of ethanol, and the mixture is boiled at reflux for 1½ hours. The solution is concentrated, diluted with water, and the neutral by-products are extracted with ether. The aqueous phase is then acidified with hydrochloric acid, extracted with ether, the ether extract is washed with water, dried over sodium sulphate and concentrated by evaporation. 2-isopropyl-α-oxo-5-indanacetic acid is obtained as an oil and is used for the next reaction without purification. The (1,3-dihydroxy-2-hydroxymethyl-2-propyl)ammonium salt of 2-isopropyl-α-oxo-5-indanacetic acid has a M.P. of B 145°–147°.

EXAMPLE 6

2-ethyl-6-chloro-5-indanacetic acid 2-ethyl-6-chloro-α-oxo-5-indanacetic acid methyl ester is reduced in a manner analogous to that described in Example 4. The cyclohexyl-ammmonium salt of the title compound has a M.P. of 145°–147°.

The starting material may be obtained as follows:
(a) A solution of 126 g of α-(diethylphosphono)butyric acid ethyl ester in 130 cc of ethanol is added dropwise at 0°–5°, while stirring, to a solution of sodium ethylate (from 27 g of sodium) in 450 cc of ethanol. Stirring is effected at 0°–5° for a further hour, a solution of 70 g of 4-chlorobenzaldehyde in 140 cc of ethanol is added dropwise and stirring is effected at room temperature for a further 2 hours. A solution of 140 g of potassium hydroxide in 280 cc of water is then added dropwise and the reaction mixture is heated at reflux, while stirring, for 18 hours, is concentrated, diluted with water, and the neutral by-products are extracted with ether. The alkaline, aqueous phase is acidified with concentrated hydrochloric acid while cooling, the colourless precipitate is filtered off by suction and washed with water. The crude α-ethyl-4-chlorocinnamic acid is recrystallized from methanol. M.P. 138°–140°.
(b) A solution of 44.5 g of α-ethyl-4-chlorocinnamic acid in 750 cc of ethanol is hydrogenated at 25° and a hydrogen pressure of 1 atmosphere with the addition of 0.4 g of a platinum(IV) oxide catalyst. After the take up of the calculated amount of hydrogen, filtration is effected and the solution is concentrated. The resulting α-ethyl-4-chlorodihydrocinnamic acid is recrystallized from petroleum ether and has a M.P. of 59°–61°.
(c) 2-ethyl-6-chloro-1-indanone is produced in a manner analogous to Example 3(c). B.P. 135°–145° at 0.1 mm of Hg.
(d) 2-ethyl-5-chloro-indan is produced in a manner analogous to Example 3(d). B.P. 122°–127° at 14 mm of Hg.
(e) 2-ethyl-6-chloro-α-oxo-5-indanacetic acid methyl ester is produced in a manner analogous to Example 1(c). B.P. 176°–180° at 0.15 mm of Hg.

EXAMPLE 7

2-ethyl-6-methyl-5-indanacetic acid 2-ethyl-α-oxo-6-methyl-5-indanacetic acid methyl ester is reduced in a manner analogous to that described in Example 4. The title compound has a M.P. of 103°–104°.

The starting material may be obtained as follows:
(a) α-ethyl-4-methylcinnamic acid is produced in a manner analogous to Example 6(a), from α-(diethylphosphono)butyric acid ethyl ester and 4-methylbenzaldehyde. M.P. 156°–158° (from methanol).
(b) A suspension of 91 g of α-ethyl-4-methyl-cinnamic acid in 1.5 liters of methyl-isobutyl-carbinol is added dropwise within one hour to 100 g of sodium in 250 cc of toluene at 130° while stirring well. After a further hour, sodium is no longer present and the mixture is cooled and 500 cc of water are carefully added thereto. The aqueous phase is separated and the methyl-isobutyl-carbinol phase is again extracted twice with water. The entire aqueous phase is acidified with concentrated hydrochloric acid and extracted with ether. The ether extract is washed with water, dried over sodium sulphate and evaporated. The crude α-ethyl-4-methyl-dihydrocinnamic acid is obtained as an oil and may be purified by chromatography.
(c) 2-ethyl-6-methyl-1-indanone is produced in a manner analogous to Example 3(c). M.P. 50°–52° (from hexane).
(d) 2-ethyl-5-methyl-indan is produced in a manner analogous to Example 3(d). The oily crude product is purified by chromatography on aluminium oxide/petroleum ether.
(e) 2-ethyl-α-oxo-6-methyl-5-indanacetic acid methyl ester is produced in a manner analogous to Example 1(c). B.P. 185°–190° at 0.1 mm of Hg.

EXAMPLE 8

2-methyl-5-indanacetic acid

α-oxo-2-methyl-5-indanacetic acid methyl ester is reduced in a manner analogous to that described in Example 4. The cyclohexyl-ammonium salt of the title compound has a M.P. of 175°–178°.

The starting material may be obtained as follows:
(a) α-methylcinnamic acid is produced in a manner analogous to Example 6(a), from α-(diethylphosphono)propionic acid methyl ester and benzaldehyde. M. P. 78°–80°.
(b) α-methyldihydrocinnamic acid is produced in a manner analogous to Example 7(b), oily crude product.
(c) 2-methyl-1-indanone is produced in a manner analogous to Example 3(c), oily, B.P. 170°–190°/11 mm Hg.
(d) A solution of 28.7 g of 2-methyl-1-indanone in 500 cc of ethanol is hydrogenated for 4 hours at room temperature under pressure with the addition of 2.5 g of palladium charcoal (10%) and 20 cc of concentrated hydrochloric acid. The solution is concentrated to approximately 100 cc, is diluted with water and extracted with petroleum ether. The extract is washed with water, dried over sodium sulphate and concentrated by evaporation. The resulting 2-methyl-indan is purified by chromatography on 200 g of aluminum oxide with petroleum ether.
(e) α-oxo-2-methyl-5-indanacetic acid methyl ester is produced in a manner analogous to Example 1(c). B.P. 170°/0.1 mm Hg.

EXAMPLE 9

2-ethyl-5-indanacetic acid 2-ethyl-α-oxo-5-indanacetic acid is reduced in a manner analogous to that described in Example 4. The title compound has an M.P. of 48°–50°.

The starting material may be obtained as follows:
(a) α-ethylcinnamic acid is produced in a manner analogous to Example 6(a), from α-(diethylphosphono)-butyric acid ethyl ester and benzaldehyde. M.P. 105°–180°.
(b) α-ethyldihydrocinnamic acid is produced in a manner analogous to Example 7(b), oily, B.P. 136°–140°/0.02 mm Hg.
(c) 2-ethyl-1-indanone is produced in a manner analogous to Example 3(c), oily, B.P. 127°–129°/11 mm Hg.
(d) 2-ethylindan is produced in a manner analogous to Example 8(d); the oily crude product is used as such for the next reaction.

(e) 2-ethyl-α-oxo-5-indanacetic acid methyl ester is produced in a manner analogous to Example 1(e). B.P. 170°–190°/0.05 mm Hg.

(f) 2-ethyl-α-oxo-5-indanacetic acid is produced in a manner analogous to Example 5(b) and used for the next reaction in crude state.

EXAMPLE 10

2-ethyl-6,α-dimethyl-5-indanacetic acid 2-ethyl-α-hydroxy-6,α-dimethyl-5-indanacetic acid [produced in a manner analogous to Example 1(d) and 1(e), from 2-ethyl-6-methyl-α-oxo-5-indanacetic acid methyl ester] is hydrogenated in a manner analogous to that described in Example 1. M.P. 106°–108°.

EXAMPLE 11

2-ethyl-α-methyl-5-indanacetic acid 2-ethyl-α-hydroxy-α-methyl-5-indanacetic acid [produced in a manner analogous to Example 1(d) and 1(e), from 2-ethyl-α-oxo-5-indanacetic acid methyl ester] is hydrogenated in a manner analogous to that described in Example 1. The cyclohexyl ammonium salt of the title compound has an M.P. of 182°–184°.

EXAMPLE 12

2,α-dimethyl-5-indanacetic acid

α-hydroxy-2,α-dimethyl-5-indanacetic acid [produced in a manner analogous to Example 1(d) and 1(e), from α-oxo-2-methyl-5-indanacetic acid methyl ester] is hydrogenated in a manner analogous to that described in Example 1. The cyclohexyl ammonium salt of the title compound has an M.P. of 190°–193°.

EXAMPLE 13

2-ethyl-6-chloro-α-methyl-5-indanacetic acid 2-ethyl-6-chloro-α-hydroxy-α-methyl-5-indanacetic acid [produced in a manner analogous to Example 1(d) and 1(e), from 2-ethyl-6-chloro-α-oxo-5-indanacetic acid methyl ester] is hydrogenated in a manner analogous to that described in Example 1. M.P. 113°–115°.

EXAMPLE 14

2-ethyl-2-methyl-5-indanacetic acid 2-ethyl-α-oxo-2-methyl-5-indanacetic acid methyl ester is reduced in a manner analogous to that described in Example 4. The cyclohexyl ammonium salt of the title compound has an M.P. of 149°–151°. The sodium salt of the title compound has an M.P. of 184°–188°.

EXAMPLE 15

2,2-diethyl-5-indanacetic acid 2,2-diethyl-α-oxo-5-indanacetic acid methyl ester is reduced in a manner analogous to that described in Example 4. The (1,3-dihydroxy-2-hydroxymethyl-2-propyl)ammonium salt of the title compound has an M.P. of 116°–119°.

The starting material may be obtained in a manner analogous to that described in Example 3(a) to 3(e):

(a) α,α-diethyldihydrocinnamic acid methyl ester is produced from 2-ethylbutyric acid and benzyl chloride. B.P. 140°–154°/14 mm Hg.

(b) α,α-diethyldihydrocinnamic acid is produced by boiling 85 g of the ester obtained above and 85 g of potassium hydroxide in 300 cc of dimethyl sulphoxide and 120 cc of water at reflux for 20 hours; it is used for the next reaction in crude state.

(c) 2,2-diethyl-1-indanone is purified by distillation in a bulb tube (air bath 200°/13 mm).

(d) 2,2-diethylindan, B.P. 140°–150° (air bath temperature).

(e) 2,2-diethyl-α-oxo-5-indanacetic acid methyl ester is used for the next reaction in crude state.

EXAMPLE 16

2,2-dimethyl-5-indanacetic acid 2,2-dimethyl-α-oxo-5-indanacetic acid methyl ester is reduced in a manner analogous to that described in Example 4. The cyclohexyl-ammonium salt of the title compound has an M.P. of 155°–156°.

The starting material may be obtained in a manner analogous to that described in Example 3(a) to 3(e):

(a) α,α-dimethyldihydrocinnamic acid methyl ester is produced from benzyl chloride and isobutyric acid methyl ester. B.P. 112°–126° at 14 mm Hg.

(b) α,α-dimethyldihydrocinnamic acid, M.P. 58.5°–59.5°.

(c) 2,2-dimethyl-1-indanone, M.P. 42°–43°.

(d) 2,2-dimethylindan is used for the next reaction in crude state. p0 (e) 2,2-dimethyl-α-oxo-5-indanacetic acid methyl ester is used for the next reaction in crude state.

EXAMPLE 17

6-chloro-2,2-dimethyl-5-indanacetic acid 6-chloro-2,2-dimethyl-α-oxo-5-indanacetic acid methyl ester is reduced in a manner analogous to that described in Example 4. The title compound has an M.P. of 143°–145°.

The starting material may be obtained in a manner analogous to that described in Example 3(a) to 3(e):

(a) α,α-dimethyl-4-chloro-dihydrocinnamic acid methyl ester is produced from isobutyric acid methyl ester and 4-chlorobenzyl chloride. B.P. 127°–145°/13 mm Hg.

(b) α,α-dimethyl-4-chloro-dihydrocinnamic acid, M.P. 90°–92° (from hexane).

(c) 6-chloro-2,2-dimethyl-1-indanone, M.P. 40°–42°.

(d) 5-chloro-2,2-dimethylindan, B.P. 105°–108°/13 mm Hg.

(e) 6-chloro-2,2-dimethyl-α-oxo-5-indanacetic acid methyl ester is used for the next reaction in crude state.

EXAMPLE 18

2-ethyl-6-chloro-2-methyl-5-indanacetic acid 2-ethyl-6-chloro-2-methyl-α-oxo-5-indanacetic acid methyl ester is reduced in a manner analogous to that described in Example 4. The title compound has an M.P. of 87°–89°.

The starting material may be produced in a manner analogous to that described in Example 3(a) to 3(e):

(a) α-ethyl-α-methyl-4-chloro-dihydrocinnamic acid methyl ester is produced from α-methylbutyric acid methyl ester and 4-chlorobenzyl chloride. B.P. 148°–168°/15 mm Hg.

(b) α-ethyl-4-chloro-α-methyldihydrocinnamic acid, M.P. 35°–36.5°.

(c) 2-ethyl-6-chloro-2-methyl-1-indanone, oily, used for the next reaction in crude state.

(d) 2-ethyl-5-chloro-2-methylindan, oil, used for the next reaction in crude state.

(e) 2-ethyl-6-chloro-2-methyl-α-oxo-5-indanacetic acid methyl ester, used for the next reaction in crude state.

EXAMPLE 19

2,2,6-trimethyl-5-indanacetic acid 2,2,6-trimethyl-α-oxo-5-indanacetic acid methyl ester is reduced in a manner analogous to that described in Example 4.

The starting material may be obtained in a manner analogous to that described in Example 3(a) to 3(e):

(a) α,α,4-trimethyldihydrocinnamic acid methyl ester is produced from α-bromo-p-xylene and isobutyric acid methyl ester. B.P. 120°–145°/13 mm Hg.

(b) α,α,4-trimethyldihydrocinnamic acid, M.P. 51°–53° (from petroleum ether/ether).

(c) 2,2,6-trimethylindan-1-one, used for the next reaction in crude state.

(d) 2,2,5-trimethylindan, B.P. 120°–130°/14 mm Hg.

(e) 2,2,6-trimethyl-α-oxo-5-indanacetic acid methyl ester, used for the next reaction in crude state.

The following compounds may also be produced in a manner analogous to that described in Example 4:

2-ethyl-4,7-dichloro-5-indanacetic acid (from 2-ethyl-4,7-dichloro-α-oxo-5-indanacetic acid), 2-ethyl-7-chloro-4-methyl-5-indanacetic acid (from 2-ethyl-7-chloro-4-methyl-α-oxo-5-indanacetic acid), 2-ethyl-4,7-dimethyl-5-indanacetic acid (from 2-ethyl-4,7-dimethyl-α-oxo-5-indanacetic acid).

EXAMPLE 20

2,2,α-trimethyl-5-indanacetic acid 2,2,α-trimethyl-α-hydroxy-5-indanacetic acid [produced in a manner analogous to Example 1(d) and 1(c)] is hydrogenated in a manner analogous to that described in Example 1. M.P. of the cyclohexyl-ammonium salt 180°–183° (from ethanol).

The following compounds may also be produced in a manner analogous to that described in Example 1:

2-ethyl-4,7-dichloro-α-methyl-5-indanacetic acid (from 2-ethyl-4,7-dichloro-α-hydroxy-α-methyl-5-indanacetic acid)

2,2,6,α-tetramethyl-5-indanacetic acid (from α-hydroxy-2,2,6,α-tetramethyl-5-indanacetic acid).

EXAMPLE 21

2-ethyl-6-chloro-2-methyl-5-indanacetic acid methyl ester

A solution of 5.2 g of 2-ethyl-6-chloro-2-methyl-α-oxo-5-indanacetic acid methyl ester in 100 cc of methanol and 10 cc of concentrated sulphuric acid is hydrogenated at 45° and a hydrogen pressure of 5 atmospheres with the addition of 1.0 g of platinum(IV) oxide. After the take up of the theoretic amount of hydrogen the catalyst is filtered off, the solution is diluted with a 5% sodium bicarbonate solution and extracted with ether. The extract is washed with water, dried over sodium sulphate and concentrated by evaporation. The resulting title compound is purified by chromatography. Thin layer chromatogram: Rf value 0.60 (adsorbent: silica gel, eluant: chloroform).

The following 5-indanacetic acid alkyl ester derivatives may be obtained in a manner analogous to that described in Example 21, by catalytic hydrogenation of the corresponding α-oxo-5-indanacetic acid alkyl ester derivatives:

2-ethyl-5-indanacetic acid methyl ester, B.P. 145° at 0.01 mm of Hg, 2-ethyl-5-indanacetic acid ethyl ester, B.P. 102°–106° at 0.01 mm of Hg, 2-ethyl-2,6-dimethyl-5-indanacetic acid methyl ester, 2-ethyl-2,6-dimethyl-5-indanacetic acid methyl ester, 2-isopropyl-5-indanacetic acid ethyl ester, 2-ethyl-6-chloro-5-indanacetic acid methyl ester, 2-ethyl-6-methyl-5-indanacetic acid methyl ester, 2-methyl-5-indanacetic acid methyl ester, 2-ethyl-5-indanacetic acid methyl ester, 2-ethyl-2-methyl-5-indanacetic acid methyl ester, 2,2-diethyl-5-indanacetic acid methyl ester, 2,2-dimethyl-5-indanacetic acid methyl ester, 6-chloro-2,2-dimethyl-5-indanacetic acid methyl ester, 2,2,6-trimethyl-5-indanacetic acid methyl ester, 2-ethyl-4,7-dichloro-5-indanacetic acid n-butyl ester, 2-ethyl-7-chloro-4-methyl-5-indanacetic acid n-propyl ester, 2-ethyl-4,7-dimethyl-5-indanacetic acid ethyl ester.

EXAMPLE 22

2-ethyl-2,α-dimethyl-5-indanacetic acid methyl ester

A solution of 8 g of 2-ethyl-α-hydroxy-2,α-dimethyl-5-indanacetic acid methyl ester in 100 cc of methanol and 8 cc of concentrated sulphuric acid is hydrogenated at 40° to 45° and a hydrogen pressure of 4 atmospheres with the addition of 0.8 g of platinum(IV) oxide. After the take up of the theoretic amount of hydrogen, the solution is filtered, diluted with a 5% sodium bicarbonate solution and extracted with ether. The extract is washed with water, dried over sodium sulphate and concentrated by evaporation. The resulting oily title compound is purified by distillation. B.P. 138°–140° at 0.3 mm of Hg.

The following α-alkyl-5-indanacetic acid alkyl ester derivatives may be obtained in a manner analogous to that described in Example 22, by catalytic hydrogenation of the corresponding α-alkyl-α-hydroxy-5-indanacetic acid alkyl ester derivatives:

2-ethyl-2,α-dimethyl-5-indanacetic acid ethyl ester, 2,2,6,α-tetra-5-indanacetic acid methyl ester, 2-isopropyl-α-methyl-5-indanacetic acid methyl ester, 2-isopropyl-α-methyl-5-indanacetic acid ethyl ester, 2-ethyl-6,α-dimethyl-5-indanacetic acid methyl ester, 2-ethyl-α-methyl-5-indanacetic acid methyl ester, 2,α-dimethyl-5-indanacetic acid methyl ester, 2-ethyl-6-chloro-α-methyl-5-indanacetic acid methyl ester, 2,2,α-trimethyl-5-indanacetic acid methyl ester, 2-ethyl-4,7-dichloro-α-methyl-5-indanacetic acid methyl ester, 2-ethyl-2,α-dimethyl-5-indanacetic acid n-butyl ester.

EXAMPLE 23

2-ethyl-5-indanacetic acid [process variant (b)]

12.8 g of 2-ethyl-5-indan-acetonitrile are dissolved in 350 cc of ethanol, a solution of 26.7 g of potassium hydroxide in 45 cc of water is added, and the mixture is boiled at reflux for 20 hours. The solution is concentrated to 50 cc, diluted with water and extracted with ether, and the ether phase is discarded. The aqueous phase is then acidified with 2 N hydrochloric acid and extracted with ether. The crude 2-ethyl-5-indanacetic acid, obtained after concentrating the ether extract, is purified by chromatography on a 50-fold quantity of silica gel using chloroform containing 1.5% of methanol as eluant. After recrystallization from hexane the title compound has a M.P. of 44°–46°.

The starting material may be obtained as follows:

(a) A mixture of 10.0 g of 2-ethyl-indan, 7.12 cc of a 40% aqueous formaldehyde solution and 14.2 cc of concentrated hydrochloric acid is stirred at 70°. 9.8 cc of concentrated sulphuric acid are added dropwise within 6 hours and the mixture is stirred at 70° for a further 2 days. Working up is effected by adding water to the cooled reaction mixture and extracting with ether. The extract is washed twice with an 8% sodium bicarbonate solution and once with water, is dried over sodium sulphate, the solvent is removed by evaporation and the 2-ethyl-5-chloromethyl-indan, obtained as oily crude product, is used as such for the next reaction.

(b) 12.0 g of the oily crude product obtained above are dissolved in 350 cc of acetone, the solution is boiled while stirring, and a solution of 17.6 g of sodium cyanide in 35 cc of water is added dropwise. The reaction mixture is boiled at reflux for 20 hours, is cooled to 25° and concentrated by evaporation in a vacuum. The residue is diluted with water and extracted with ether. The extract is washed with water, dried over sodium sulphate and concentrated by evaporation, whereby crude 2-ethyl-5-indan-acetonitrile is obtained as an oil, which is purified by distillation. B.P. 131°–135° at 0.12 mm of Hg.

The 5-indanacetic acid derivatives described in Examples 1–19 may be produced in a manner analogous to that described in Example 23, from the corresponding 5-indan-acetonitrile derivatives produced in a manner analogous to Example 23(a) and 23(b).

EXAMPLE 24

2-ethyl-5-indanacetic acid ethyl ester

A solution of 12.0 g of purified 2-ethyl-5-indan-acetonitrile in 200 cc of ethanol is saturated with hydrogen chloride gas while cooling with ice. The solution is subsequently boiled at reflux for 20 hours, concentrated by evaporation and again dissolved in 170 cc of ethanol. 4.7 cc of water are subsequently added and the solution is boiled at reflux for 3 hours, concentrated by evaporation, and the residue is distributed between benzene and water. The benzene phase is washed with a 5% sodium bicarbonate solution and water, is dried over sodium sulphate and concentrated by evaporation. The title compound obtained as oily residue is distilled in a bulb tube. B.P. 102°–106° at 0.01 mm of Hg.

The remaining 5-indanacetic acid alkyl ester derivatives mentioned in Examples 21 and 22 may also be obtained in a manner analogous to that described in Example 24, by solvolysis of the corresponding 5-indan-acetonitrile derivatives.

EXAMPLE 25

2-ethyl-6-chloro-2-methyl-5-indanacetic acid [process variant (d)]

A solution of 20 g of potassium hydroxide in 40 cc of water is added to a solution of 11.5 g of 2-ethyl-6-chloro-2-methyl-5-indanacetic acid methyl ester in 250 cc of methanol, and the solution is boiled at reflux for one hour. The cooled solution is concentrated, diluted with water and the neutral components are extracted with ether. The aqueous phase is acidified with hydrochloric acid, extracted with ether, the ether extract is washed with water, dried over sodium sulphate and concentrated by evaporation. The resulting 2-ethyl-6-chloro-2-methyl-5-indanacetic acid is recrystallized from hexane and has a M.P. of 87°–89°.

EXAMPLE 26

2,2,α-trimethyl-5-indanacetic acid [process variant (d)]

17 g of 2,2,α-trimethyl-5-indanacetic acid methyl ester are saponified together with 8.2 g of potassium hydroxide in 160 cc of methanol and 16 cc of water in a manner analogous to that described in Example 25. After working up the reaction mixture, oily 2,2,α-trimethyl-5-indanacetic is obtained. The cyclohexylammonium salt of the title compound has a M.P. of 180°–183° (from ethanol).

The 2,2,α-trimethyl-5-indanacetic acid methyl ester, used as starting material, is obtained as follows: [process variant (c)]

A solution of 19.6 g of 2,2-dimethyl-5-indanacetic acid methyl ester in 50 cc of tetrahydrofuran is added dropwise, at −70°, to a solution of lithium diisopropylamide (produced from a solution of 13.1 g of diisopropylamine in 200 cc of tetrahydrofuran and 50 cc of a 2.5 M solution of n-butyl-lithium in hexane) within 30 minutes while stirring, and stirring is then continued at −70° for 30 minutes. A solution of 71 g of methyl iodide in 50 cc of tetrahydrofuran is then added dropwise within 30 minutes, the solution is stirred at −30° to −40° for 3 hours, is heated to room temperature and concentrated. The product is diluted with water and extracted with ether. The ether portions are washed with a 2% hydrochloric acid solution, dried over sodium sulphate and concentrated. The crude product is distilled in a bulb tube at 135° at 0.03 mm of Hg, and the resulting 2,2,α-trimethyl-5-indanacetic acid methyl ester is again distilled at 0.5 mm of Hg. B.P. 134°–138° at 0.5 mm of Hg.

The 5-indanacetic acid derivatives described in Examples 1 to 19 may also be obtained in a manner analogous to that described in Example 25 or 26, by hydrolysis of the corresponding 5-indanacetic acid alkyl ester derivatives.

The compounds of formula I are useful as antiphlogistic agents e.g. for the inhibition of exudation in oedemas as indicated by an inhibition of oedema formation in rats in the carrageen paw oedema test in vivo on p.o. administration of from about 20 to about 100 mg/kg animal body weight of the compounds.

For this use the dosage will, of course, vary depending on the compound employed, mode of administration and treatment desired. However, in general, satisfactory results are obtained when administered at a daily dosage of from about 20 mg to about 100 mg/kg animal body weight, conveniently given in divided doses 2 to 4 times a day or in sustained release form. For the larger mammals, the total daily dosage is in the range from about 200 mg to about 2000 mg, and dosage forms suitable for oral administration comprise from about 50 mg to about 1000 mg of the compounds admixed with a solid or liquid pharmaceutical carrier or diluent.

The compounds of formula I are furthermore useful as anti-arthritis agents, as indicated by an inhibition of swellings in the Freund adjuvant arthritis latent period test in rats on p.o. administration of from about 20 to about 100 mg/kg animal body weight of the compounds.

For this use the dosage will, of course, vary depending on the compound employed, mode of administration and treatment desired. However, in general, satisfactory results are obtained when administered at a daily dosage of from about 30 mg to about 100 mg/kg animal body weight, conveniently given in divided doses 2 to 4 times a day or in sustained release form. For the larger mammals, the total daily dosage is in the range from about 200 mg to about 2000 mg, and dosage forms suitable for oral administration comprise from about 50 mg to about 1000 mg of the compounds admixed with a solid or liquid pharmaceutical carrier or diluent.

The compounds of formula I wherein $R_3$ is hydrogen may be administered in pharmaceutically acceptable salt form. Such salt forms exhibit the same order of activity as the free forms. Representative salt forms include alkali metal salts such as the sodium or potassium salt, alkaline earth metal salts such as the calcium salt and also include organic salts such as the ammonium salt and amine salts such as the dimethylamine, diethylamine, trimethylamine and benzylamine salts. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in table form may be coated by conventional techniques to delay disintegration of the tablet and absorption of the active ingredient in the gastrointestinal tract and thereby provide sustained action over a long period.

The Example 1 compound is particularly interesting.

In one group of compounds $R_5$, $R_6$ and $R_7$ are all hydrogen. In a sub-group $R_2$, $R_3$ and $R_4$ are hydrogen. In another group of compounds one of $R_5$, $R_6$ and $R_7$ is chlorine and the other two of $R_5$, $R_6$ and $R_7$ are hydrogen. Preferably $R_6$ and $R_7$ are the same.

I claim:

1. A compound of formula I,

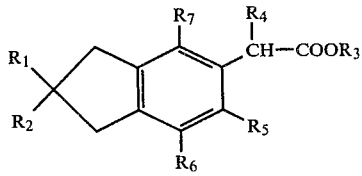

wherein
$R_1$ is lower alkyl,
$R_2$ is hydrogen or lower alkyl,
$R_3$ is hydrogen,
$R_4$ is hydrogen or lower alkyl,
$R_5$ is chlorine or lower alkyl, and each of
$R_6$ and $R_7$ is hydrogen, or,
  $R_5$ is hydrogen, and $R_6$ and $R_7$ are independently hydrogen, chlorine or lower alkyl, or alternatively in pharmaceutically acceptable salt form.

2. A method of treating arthritis in animals, which comprises administering to an animal in need of such treatment a therapeutically effective amount of a compound of claim 1.

3. A method of treating exudation in inflammations and oedemas in animals, which comprises administering to an animal in need of such treatment a therapeutically effective amount of a compound of claim 1.

4. A pharmaceutical composition for treating arthritis or exudation in inflammations and oedemas in animals, comprising an effective amount of a compound of claim 1 in association with a pharmaceutical carrier or diluent.

5. A compound of claim 1 wherein $R_6$ and $R_7$ are the same.

6. A compound of claim 1 wherein $R_1$ is methyl, ethyl or isopropyl.

7. A compound of claim 1 wherein $R_2$ is hydrogen or methyl.

8. A compound of claim 1 wherein $R_4$ is hydrogen or methyl.

9. A compound of claim 1 wherein $R_5$, $R_6$ and $R_7$ are all hydrogen.

10. A compound of claim 1 wherein one of $R_5$, $R_6$ and $R_7$ is hydrogen or chlorine and the other two of $R_5$, $R_6$ and $R_7$ are hydrogen.

11. A compound of claim 1 wherein $R_2$ to $R_7$ are all hydrogen.

12. The compound of claim 1 which is 2-isopropyl-$\alpha$-methyl-5-indanacetic acid.

13. The compound of claim 1 which is 2-ethyl-2,$\alpha$-dimethyl-5-indanacetic acid.

14. The compound of claim 1 which is 2-ethyl-2,6-dimethyl-5-indanacetic acid.

15. The compound of claim 1 which is 2-isopropyl-5-indanacetic acid.

16. The compound of claim 1 which is 2-ethyl-6-chloro-5-indanacetic acid.

17. The compound of claim 1 which is 2-ethyl-6-methyl-5-indanacetic acid.

18. The compound of claim 1 which is 2-methyl-5-indanacetic acid.

19. The compound of claim 1 which is 2-ethyl-5-indanacetic acid.

20. The compound of claim 1 which is 2-ethyl-6,$\alpha$-dimethyl-5-indanacetic acid.

21. The compound of claim 1 which is 2-ethyl-$\alpha$-methyl-5-indanacetic acid.

22. The compound of claim 1 which is 2,$\alpha$-dimethyl-5-indanacetic acid.

23. The compound of claim 1 which is 2-ethyl-6-chloro-$\alpha$-methyl-5-indanacetic acid.

24. The compound of claim 1 which is 2-ethyl-2-methyl-5-indanacetic acid.

25. The compound of claim 1 which is 2,2-diethyl-5-indanacetic acid.

26. The compound of claim 1 which is 2,2-dimethyl-5-indanacetic acid.

27. The compound of claim 1 which is 6-chloro-2,2-dimethyl-5-indanacetic acid.

28. The compound of claim 1 which is 2-ethyl-6-chloro-2-methyl-5-indanacetic acid.

29. The compound of claim 1 which is 2,2,6-trimethyl-5-indanacetic acid.

30. The compound of claim 1 which is 2,2α-trimethyl-5-indanacetic acid.

31. The compound of claim 1 which is 2-ethyl-4,7-dichloro-5-indanacetic acid.

32. The compound of claim 1 which is 2-ethyl-7-chloro-4-methyl-5-indanacetic acid.

33. The compound of claim 1 which is 2-ethyl-4,7-dimethyl-5-indanacetic acid.

34. The compound of claim 1 which is 2-ethyl-4,7-dichloro-α-methyl-5-indanacetic acid.

35. The compound of claim 1 which is 2,2,6,α-tetramethyl-5-indanacetic acid.

36. A compound of the formula

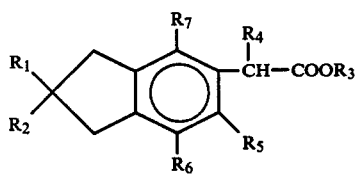

wherein
$R_1$ is lower alkyl,
$R_2$ is hydrogen or lower alkyl,
$R_3$ is hydrogen,
$R_4$ is hydrogen or lower alkyl,
$R_5$ is lower alkyl,
and each of $R_6$ and $R_7$ is hydrogen, or $R_5$ is hydrogen, and $R_6$ and $R_7$ are independently hydrogen or lower alkyl, or alternatively in pharmaceutically acceptable salt form.

37. A composition comprising a therapeutically effective amount of a compound of claim 36, to treat arthritis or exudations in inflammations and edemas in animals, and a pharmaceutically acceptable carrier therefor.

38. A method of treating arthritis or exudations in inflammations and edemas in animals which comprises the administering thereto of a therapeutically effective amount of a compound of claim 36.

39. A compound of the formula

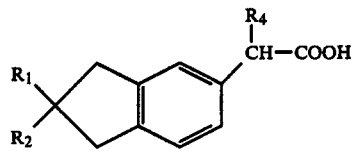

wherein
$R_1$ is methyl, ethyl or isopropyl;
$R_2$ is hydrogen or methyl; and
$R_4$ is methyl or hydrogen; or a pharmaceutically acceptable salt thereof.

40. A compound of the formula wherein
$R_1$ is alkyl of 1–4 carbon atoms;
$R_2$ is hydrogen and
$R_4$ is methyl or a pharmaceutically acceptable salt thereof.

* * * * *